United States Patent [19]

Berg et al.

[11] Patent Number: 5,762,637

[45] Date of Patent: Jun. 9, 1998

[54] INSERT MOLDED CATHETER TIP

[75] Inventors: Todd A. Berg, Lino Lakes; Bruce Ebner, Shorewood, both of Minn.

[73] Assignee: SciMed Life Systems, Inc., Maple Grove, Minn.

[21] Appl. No.: 703,641

[22] Filed: Aug. 27, 1996

[51] Int. Cl.[6] .................................................. A61M 5/00
[52] U.S. Cl. ........................... 604/264; 604/280; 604/282
[58] Field of Search ............................... 604/264, 265, 604/280, 282, 283, 905

[56] References Cited

U.S. PATENT DOCUMENTS

| | | |
|---|---|---|
| 3,470,869 | 10/1969 | Fenton et al. . |
| 3,725,522 | 4/1973 | Sheridan et al. . |
| 3,865,666 | 2/1975 | Shoney . |
| 3,873,391 | 3/1975 | Plauka et al. . |
| 3,959,429 | 5/1976 | Benning . |
| 3,985,601 | 10/1976 | Panagrossi . |
| 3,989,571 | 11/1976 | Harautuneian . |
| 4,085,185 | 4/1978 | Adair . |
| 4,093,484 | 6/1978 | Harrison et al. . |
| 4,207,900 | 6/1980 | Patel et al. . |
| 4,210,478 | 7/1980 | Shoney . |
| 4,284,459 | 8/1981 | Patel et al. . |
| 4,328,056 | 5/1982 | Snooks . |
| 4,531,943 | 7/1985 | Van Tassel et al. ............ 604/280 |
| 4,557,781 | 12/1985 | Hoppie . |
| 4,596,563 | 6/1986 | Pande ........................ 604/264 |
| 4,655,762 | 4/1987 | Rogers ....................... 604/905 |
| 4,737,219 | 4/1988 | Taller et al. . |
| 4,753,765 | 6/1988 | Pande . |
| 4,778,550 | 10/1988 | Barton et al. . |
| 4,806,182 | 2/1989 | Rydell et al. . |
| 4,826,480 | 5/1989 | Diaz et al. .................. 604/280 |
| 4,842,590 | 6/1989 | Tanabe et al. ............... 604/282 |
| 4,863,442 | 9/1989 | DeMello et al. ............. 604/282 |
| 4,874,373 | 10/1989 | Luther et al. ................ 604/164 |
| 4,886,506 | 12/1989 | Lovgren et al. .............. 604/280 |
| 4,950,257 | 8/1990 | Hibbs et al. ................. 604/265 |
| 4,959,067 | 9/1990 | Muller ....................... 606/190 |
| 5,035,686 | 7/1991 | Crittenden et al. ........... 604/96 |
| 5,125,913 | 6/1992 | Quackenbush ............... 604/264 |
| 5,160,559 | 11/1992 | Scovil et al. . |
| 5,167,647 | 12/1992 | Wijkamp et al. ............. 604/281 |
| 5,190,529 | 3/1993 | McCrory et al. ............. 604/175 |
| 5,201,723 | 4/1993 | Quinn ........................ 604/264 |
| 5,217,555 | 6/1993 | Franklin, III et al. . |
| 5,221,270 | 6/1993 | Parker ....................... 604/282 |
| 5,240,537 | 8/1993 | Bodicky . |
| 5,254,107 | 10/1993 | Soltesz ...................... 604/282 |
| 5,279,596 | 1/1994 | Castaneda et al. ........... 604/282 |
| 5,300,032 | 4/1994 | Hibbs et al. ................. 604/164 |
| 5,312,356 | 5/1994 | Engelson et al. ............. 604/164 |
| 5,318,032 | 6/1994 | Lonsbury et al. ............ 128/658 |
| 5,330,444 | 7/1994 | Webler et al. ............... 604/265 |
| 5,380,301 | 1/1995 | Prichard et al. ............. 604/281 |
| 5,533,988 | 7/1996 | Dickerson et al. ........... 604/282 |
| 5,545,151 | 8/1996 | O'Connor et al. ........... 604/282 |
| 5,569,218 | 10/1996 | Berg ......................... 604/280 |

FOREIGN PATENT DOCUMENTS

| | | |
|---|---|---|
| 0 437 291 B1 | 12/1993 | European Pat. Off. . |
| 2 187 670 | 9/1987 | United Kingdom . |

Primary Examiner—Mark Bockelman
Assistant Examiner—Jennifer R. Sadula
Attorney, Agent, or Firm—Nawrocki, Rooney & Sivertson, P.A.

[57] ABSTRACT

A catheter incorporating an insert molded tip and an improved method of manufacture that is simple, efficient, and significantly reduces current scrap rates for soft tip attachment to catheters. One catheter shaft embodiment includes a counterbored distal portion having anchor holes through the wall of the catheter body in this distal portion. In another embodiment, the catheter shaft has a reduced diameter portion including anchor holes. In yet another embodiment the catheter shaft has external longitudinal and external grooves. The tip is injection molded onto the body with tip material filling the counterbore, reduced diameter portion, anchor holes, and grooves to form integral anchors to secure the tip.

10 Claims, 2 Drawing Sheets

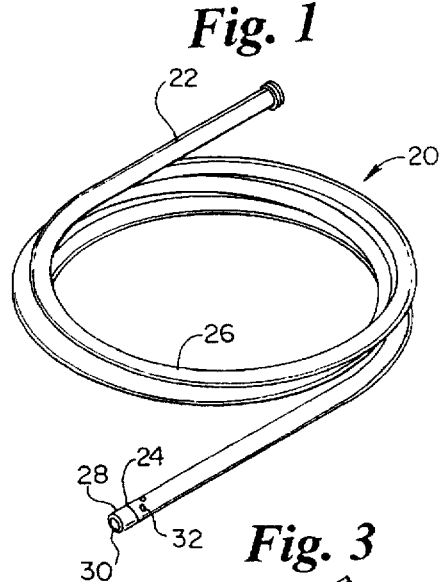
Fig. 1
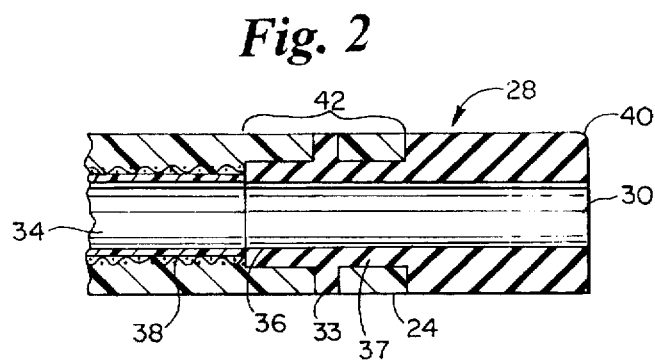
Fig. 2
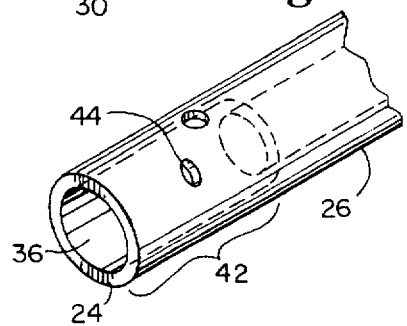
Fig. 3
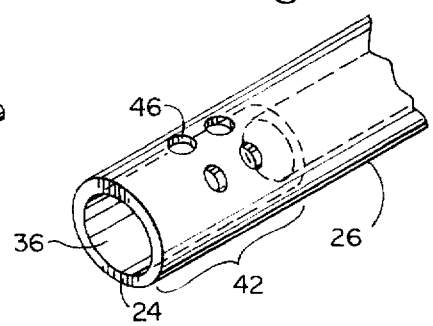
Fig. 4
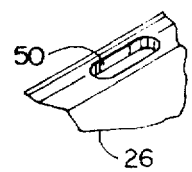
Fig. 5
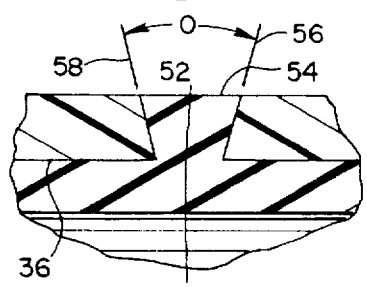
Fig. 6
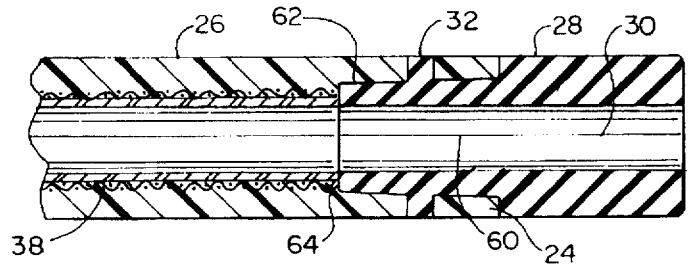
Fig. 7
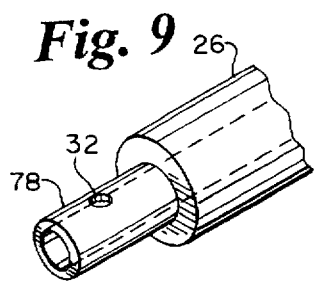
Fig. 9
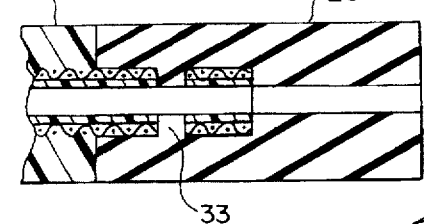
Fig. 10
Fig. 12

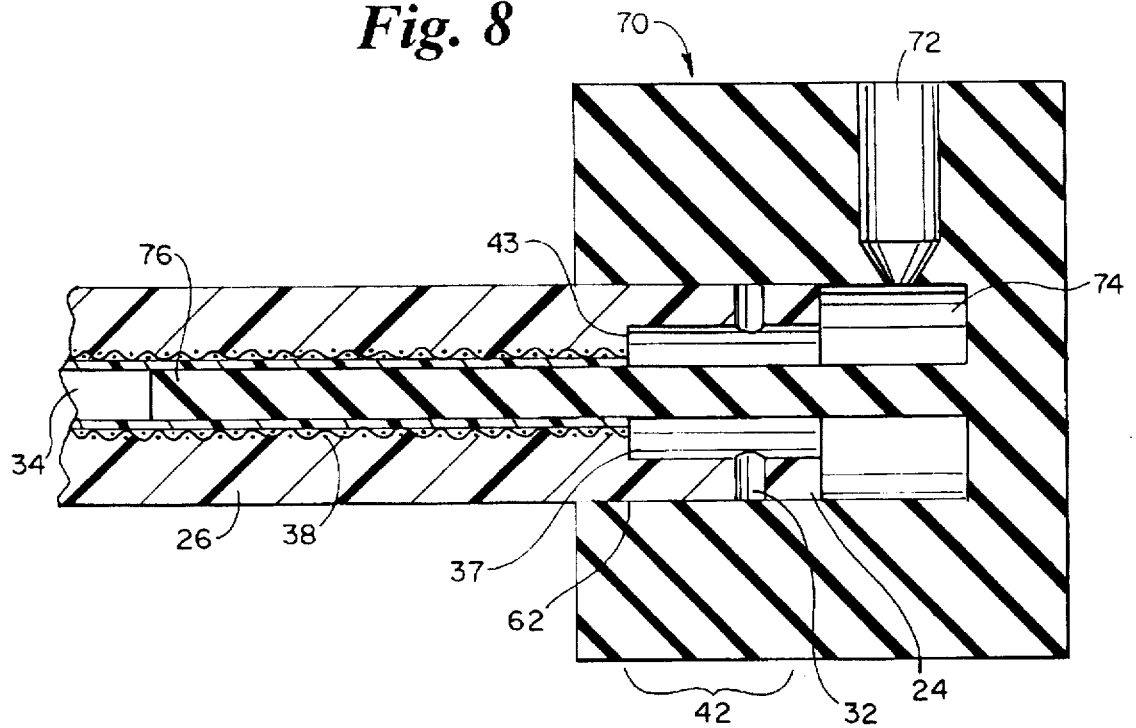
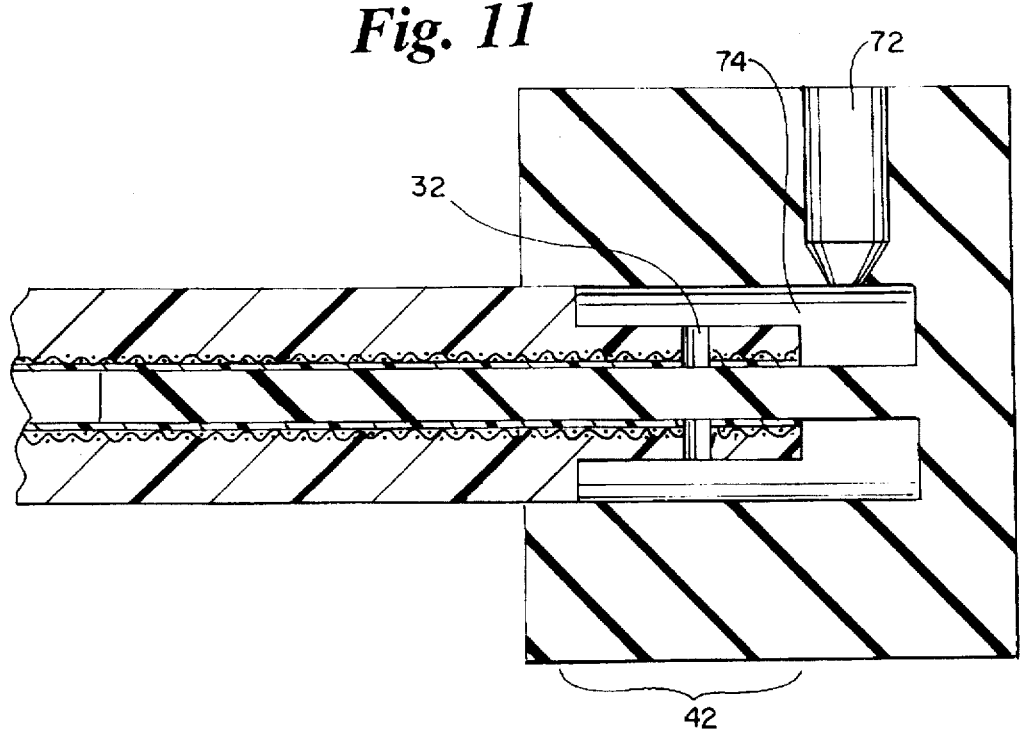

INSERT MOLDED CATHETER TIP

FIELD OF THE INVENTION

The present invention relates to guide and diagnostic catheters having soft deformable tips for use in intravascular procedures. In particular, the present invention relates to an improved guide and diagnostic catheter tip and method of manufacture, wherein the tip is insert molded to the distal end of the catheter which includes recesses such as anchor holes and grooves which are filled with injected tip material to integrally secure the tip to the catheter shaft.

DESCRIPTION OF THE PRIOR ART

Many medical procedures include the insertion of a catheter into a lumen of a living body. In the performance of such medical procedures, guide catheters and diagnostic catheters are well known for use in catheterization procedures in the vascular system, such as angiography, angioplasty, and other diagnostic or interventional procedures.

For example, diagnostic catheters are used for procedures including dye delivery, arterial flushing or arterial pressure monitoring. Diagnostic catheters are also used during cardiac catheterization for diagnosis of coronary artery disease, for defining vessel anatomy, for isolating lesions, and for identifying adjacent cardiac branches which may impinge on a lesion and affect ventricular function. For procedures within the coronary artery, the distal end of the diagnostic catheter is inserted percutaneously into the vascular system of the patient and pushed distally up and over the aortic arch. A proximal end of the catheter protrudes outside of the patient's body and may be used for implementation of diagnostic procedures, such as dye delivery, flushing, and arterial pressure monitoring.

A diagnostic catheter generally includes a shaft with a lumen extending from the proximal end of the shaft to the distal end. Connected to the distal end of the shaft is a soft tip.

Angioplasty is widely used for the treatment of coronary disease. Angioplasty makes use of guide catheters to provide an access to the area within the arterial system for opening a stenosis in the artery or other parts of the vascular system. Guide catheters aid in treatment of arterial blockage and arterial lesions by providing a conduit for positioning interventional systems at a treatment site.

Guide catheters are similar in construction to diagnostic catheters, although they are generally larger in size. A lumen extends longitudinally through the guide catheter shaft from the proximal to the distal end. A soft tip is connected to the distal end of the guide catheter shaft. As with diagnostic catheters, the guide catheter is also inserted into the vascular system of the patient percutaneously. Here, the distal end of the guide catheter is pushed distally up through the vascular system until the guide catheter soft tip is properly engaged in the ostium of the coronary artery or graft. The proximal end of the guide catheter protrudes outside of the patient's body providing access for delivery of the interventional systems.

It is preferred that guide catheters be manufactured with a relatively stiff proximal section and a softer tip section. The stiffer proximal section prevents kinking of the tube, while allowing the tube to be pushed along a path in the vascular system. The softer tip provides less traumatic contact with vessel walls. To meet these requirements, guide catheters and diagnostic catheters having various designs have been proposed and utilized.

Several methods for attaching the soft tip to the rigid catheter body have also been proposed. Typical prior art manufacturing procedures involve extruding catheter material over an elongated cylindrical core having a uniform diameter, then removing the catheter from the core to prepare the distal end to receive a soft tip. Typically the soft tips are attached by chemical bonding, such as adhesion or by thermal bonding, such as fusion of a soft tip material to the distal end of the catheter. The thermal bonding process involves applying sufficient heat to thermally fuse the catheter and the soft tip components together. With this process, however, the braided wires incorporated into the tube can become exposed at the catheter surface after the thermal bonding process is complete. This typically results in a catheter which must be discarded. This concern is more prevalent when high strength bonding wire, such as hardened stainless steel, is used.

Shoney (U.S. Pat. No. 4,210,478) discloses a method of manufacturing a catheter having a soft tip, wherein the catheter tip is injection molded to the shaft. Shoney discloses a significant characteristic of the process resides in the fact that when the balloon is molded, it is simultaneously bonded to the catheter shaft. The molding of the balloon or tip and the securement of the balloon or tip to the shaft occurs simultaneously. Shoney clearly relies on the adhesion properties of the materials of the shaft relative to the material of the tip to form the bond which secures the tip to the shaft.

Wijkamp et al. (European Patent Publication 0 437 291 B1) disclose another method of injection molding a tip onto a catheter shaft. Wijkamp et al. disclose that when the end portion or tip is injection molded in liquid form, at least a portion of the heated liquid plastic moves against the end surface of the basic or tubular body. This end surface is well heated and the material thereof at the location of the end surface will become fused with the material of the tip or end portion. The basic body is preferably manufactured from a thermoplastic, the material thereof at the location of the end surface can therefore likewise melt as a result of the flow of heated plastic and mix with this flow so that a very good joint results. Wijkamp et al. therefore rely on the bonding capabilities between the two material to form a secure joint.

Thermal and adhesive bonding of tips, whether subsequent to manufacture of each part or when injection molding a tip onto a shaft, also limits the combination of materials which may be used for each component. Many polymers are not compatible with each other, in that they do not thermally bond nor will an adhesive work to adhere many combinations. Another limitation of the current process for attaching the soft tip to the catheter shaft is the requirement of many components and processes to accomplish the actual bonding step. These include bonding mandrels, bonding sleeves, tip extrusion, tip grinding, tip cutting, and core removal. Further, with thin-walled catheters, bond strengths are limited by the wall thickness.

It is desirable to have a soft tip design and manufacturing process which allows use of any combination of polymeric materials and is less labor intensive with a reduced catheter scrap rate. Specifically, a soft tip manufacturing method is needed that will be compatible with dissimilar materials and eliminate the bonding mandrel and bonding sleeve components, while significantly reducing the current catheter scrap rates and reducing the current manufacturing costs. In addition, the manufacturing method must be compatible with high strength wire designs, thin-walled catheter designs, and all catheter French sizes.

SUMMARY OF THE INVENTION

The present invention is a guide or diagnostic catheter having a soft distal tip which is injection molded onto the catheter body. To secure the tip to the body in one embodiment, a plurality of anchor holes are pre-bored through the catheter body wall in a counterbored distal section. These anchor holes fill with polymeric material as the tip is injection molded onto the body. In another embodiment, external longitudinal and annular grooves are formed in the catheter distal section. When cooled, the anchors, ribs, and rings formed within such holes and grooves become an integral part of the soft tip and secure the soft tip in place to the catheter body adding mechanical strength to the thermal bond without adhesive. Due to the above-mechanical anchoring of the tip, thermal bond strength is less important and allows bonding of dissimilar materials as needed (i.e., a nylon shaft to a polyurethane tip). A further advantage derived from the anchor holes is the ability to visually inspect the degree of filling of such holes upon injection of tip material. This provides a visual measure of the adequacy of the securing of the tip. The present invention also relates to the method of manufacturing the catheter with an anchored tip, which eliminates the use of bonding mandrels and bonding sleeve components and significantly reduces catheter scrap rates. In addition, the present invention is compatible with high strength braid wire designs, thin-walled catheter designs, and all catheter French sizes.

In a preferred embodiment, the catheter assembly of the present invention is for use as a guide or diagnostic catheter. The catheter includes a catheter body and a tip. The catheter body includes a generally elongate tubular shaft having a proximal end and a distal end, with a lumen extending longitudinally between the proximal end and the distal end. A distal portion of the catheter body is counterbored so that the lumen diameter is larger in the distal portion than the rest of the length of the catheter body. Thus, the catheter body includes a radial shoulder at the axial location where the distal portion begins due to the step change in lumen diameter.

In another preferred embodiment, a distal portion of the catheter body is stripped to form a reduced diameter portion, such that the lumen diameter remains unchanged. Thus, the catheter body includes a radial shoulder at the axial location where the distal reduced diameter portion begins due to the step decrease in catheter shaft diameter.

The catheter has a soft tubular tip having a proximal end which extends into the distal portion of the catheter body, and also extends distally beyond the distal end of the catheter body. The soft tubular tip has an outside diameter substantially equal to the outside diameter of the tubular shaft, and an inside diameter substantially equal to the diameter of the lumen proximal of the distal portion. The portion of the soft tubular tip extending into the distal portion of the catheter body fills the volume created by the counterbored larger lumen diameter or the reduced diameter portion of the above embodiments.

The catheter body also has one or more anchor holes extending generally perpendicular to the longitudinal axis of the tubular shaft, and located within the distal portion of the catheter body. The portion of the soft tubular tip extending into the distal segment of the catheter shaft flows into and fills the anchor holes and secures the soft tubular tip to the catheter body. In a preferred embodiment, the soft tubular tip is injection molded into the end portion of the tubular shaft and the anchor holes fill during this process to form integral anchors.

In another preferred embodiment, the one or more anchor holes can be configured in a variety of shapes, bore depths and locations along the distal portion of the tubular shaft. The anchor holes can have a circular or slotted shape, or any other shape desired. To provide additional strength in securing the soft tubular tip to the tubular shaft, the anchor holes can be slightly angled. With this configuration, the anchor holes would have a larger diameter at the outside surface of the catheter body than at the inside surface within the catheter body. The angled hole more securely holds the soft tubular tip within the tubular catheter shaft.

The anchor holes can be located anywhere and in any relative position within the counterbore or reduced diameter of the distal portion of the catheter body. For example, two anchor holes could be used such that their locations relative to the distal end of the catheter body are different. Four holes could be used at any location, such that each pair of holes have a location which is the same distance from the distal end of the tubular shaft, and the two pairs each have a different distance from the distal end of the tubular shaft. In fact, any combination or location of holes can be used to secure the soft tubular tip to the tubular shaft.

In another embodiment of the invention, the distal portion of the catheter shaft includes a reduced diameter portion. This reduced diameter portion has anchor holes. The portion of the soft tubular tip extending into the distal portion of the catheter shaft protrudes into the volume created by the reduced diameter and further into the anchor holes therein.

In yet another embodiment of the invention, the distal portion of the catheter shaft has an external annular groove contiguous with external longitudinal grooves extending from the annular groove to the distal end of the catheter. The portion of the soft tubular tip extending over the distal portion of the catheter shaft protrudes into the volume created by the external longitudinal grooves forming longitudinal ribs, and further into the external annular groove, forming a retaining ring. The retaining ring overlaps the distal shoulder of the annular groove, securing the soft tubular tip to the tubular catheter shaft.

The present invention also includes a method of manufacturing the above described soft tip catheter. The method includes the steps of providing a generally elongate tubular catheter shaft having a proximal end and a distal end with a lumen extending longitudinally between the proximal end and the distal end. The distal end of the tubular shaft has a distal portion including a counterbore with a selected depth along the axis of the lumen within which the lumen steps to a larger diameter. Another embodiment calls for providing a tubular catheter shaft having a distal reduced diameter portion. Yet another embodiment requires a tubular catheter shaft having an external annular groove contiguous with longitudinal grooves extending to the catheter shaft distal end.

The method can further include boring one or more anchor holes through the catheter body within the distal counterbored or reduced diameter portion of the catheter body where the holes extend generally perpendicular to the longitudinal axis of the catheter shaft.

The distal end of the catheter shaft is then inserted part of the way into a mold cavity having a diameter substantially equal to the outside diameter of the catheter body. Generally, the entire distal portion of the catheter body is inserted into the mold, and a portion of the mold cavity remains void distal of the distal end of the catheter body. The mold cavity includes a pin which extends into the lumen of the catheter body to a point proximal of the distal counterbored portion. The pin diameter is substantially equal to the lumen diameter of the tubular shaft proximal of the distal portion.

A predetermined volume of polymeric material is then injected into the mold cavity around the mandrel until the mold cavity is filled. As the mold cavity fills, the anchor hole or holes which open into the cavity, as well as any grooves, also fill with polymeric material. A soft tip is thus formed when the predetermined volume of material fills the cavity a predetermined distance beyond the distal end of the catheter body. When sufficiently cured or cooled, the catheter body and tip anchored thereto are removed from the mold cavity.

The present invention provides an improved catheter having a tip anchored thereto, and an improved method of manufacture that is simple, efficient and significantly reduces current scrap rates and manufacturing costs for soft tip attachment to catheters. This improved manufacturing method eliminates bonding mandrels and bonding sleeve components, thus reducing manufacturing costs. In addition, this method is compatible with dissimilar shaft and tip materials, as well as high strength braid wire designs, thin-walled catheter designs, and all catheter French sizes.

BRIEF DESCRIPTION OF THE DRAWINGS

The invention will be further described with reference to the accompanying drawings where like numbers refer to like parts in the several views and wherein:

FIG. 1 is a perspective view of a catheter of the present invention having a soft tip anchored thereto;

FIG. 2 is a fragmentary cross section of the distal end of the catheter showing the construction of the catheter and the soft tip;

FIG. 3 is a fragmentary perspective view of the distal portion of a catheter body illustrating two anchor holes located within the distal portion;

FIG. 4 is a fragmentary perspective view of an alternative embodiment illustrating four anchor holes located within the distal portion of the catheter body;

FIG. 5 is a partial perspective view illustrating a slotted anchor hole located within the distal portion of the catheter body;

FIG. 6 is a partial cross section showing a slightly angled anchor hole located within the distal portion of the catheter body;

FIG. 7 is a partial cross section illustrating an alternative embodiment of the present invention, wherein the counterbore diameter of the distal portion of the catheter body varies axially;

FIG. 8 is a partial cross section of the catheter and mold assembly of the present invention illustrating the method of forming the tip by injection molding;

FIG. 9 is a fragmentary perspective view of an alternative embodiment wherein the catheter shaft has a reduced diameter distal portion having an anchor hole;

FIG. 10 is a partial cross section taken through the longitudinal plane bisecting the anchor hole, further illustrating the alternative embodiment of FIG. 9;

FIG. 11 is a partial cross section of the catheter and mold assembly of the present invention illustrating the method of forming the alternative embodiment tip of FIGS. 9 and 10 by injection molding; and FIG. 12 is a fragmentary perspective view of an alternative embodiment wherein the catheter shaft has external longitudinal grooves contiguous an external annular groove.

DETAILED DESCRIPTION OF THE PREFERRED EMBODIMENTS

FIG. 1 is a perspective view of a catheter assembly 20 in accordance with the present invention. The catheter assembly 20 includes a generally elongate tubular shaft or catheter body 26 having a proximal end 22, a distal end 24, and a lumen 30 extending therethrough. A soft tubular tip 28 is attached to the distal end 24 of shaft 26, where lumen 30 continues from the soft tubular tip 28 to the proximal end 22 of shaft 26. In a preferred embodiment, two anchor holes 32 are present for securing the soft tubular tip 28 to the distal end 24 of tubular shaft 26.

In a preferred construction, the catheter body 26 includes an inner tubular member having a lumen extending therethrough. A wire braid 38 surrounds the inner tubular member to provide additional support to the catheter body. An outer tubular member is extruded over the wire braid. Thus, the catheter body 26 preferably includes two polymeric materials with a braid therebetween. The inner layer is preferably manufactured from a fluoropolymer or thermoplastic, while the outer layer is preferably manufactured from a thermoplastic such as a polyether blocked amide (PEBA). The wire braid is preferably hardened stainless steel, and is contained within the catheter shaft 26 to provide sufficient torque and kink performance to the catheter to assist in proper positioning within the vascular system.

FIG. 2 is a partial cross section of the distal end of the catheter 20 showing the construction of the catheter shaft 26 and the soft deformable tip 28 as secured by material protruding into the anchor holes 32. The catheter body lumen 30 and the lumen 34 through the tip 28 are of substantially the same diameter, and lumen 30 extends to the proximal end 22 of catheter shaft 26 as shown in FIG. 1.

The soft tubular tip 28 has a distal end 40 which extends beyond the distal end 24 of catheter shaft 26. The outside diameter of the soft tubular tip 28, which extends distally of the distal end of the catheter body 26, is substantially equal to the outside diameter of the distal end 24 of the catheter shaft 26.

The catheter body 26 includes a distal portion 42. The distal portion 42 incorporates a counterbore 37 so that the catheter body lumen 30 in the distal portion 42 is of a larger diameter. Thus, a radial shoulder 43 is formed within the lumen 30 at the proximal end of the counterbore 37.

The distal portion 42 also includes a plurality of anchor holes 32 extending generally perpendicular to the longitudinal axis of the distal portion 42 of the catheter shaft 26. As shown in FIG. 2, the material comprising the soft tubular tip 28 protrudes into the anchor holes 32 to form anchors 33, which secure the soft tubular tip 28 to the distal end 24 of catheter shaft 26. Anchor holes 32 are located at the same distance longitudinally from the distal end 24 of the catheter shaft 26 in the embodiment of FIG. 2, although this is not critical. It is, however, critical that the anchor holes 32 are located within the distal portion 42. Because the distal portion 42 defines the length where lumen 34 steps to a larger diameter lumen 36 at the distal end 24 of catheter shaft 26, the anchor holes 32 must be within this region so that the tip material which fills the large diameter lumen 36 in the counterbore 37 can also protrude into the anchor holes 32.

FIG. 3 is a fragmentary perspective view of a distal segment of the catheter body 26 illustrating an alternative arrangement of two anchor holes 44 located within the distal segment 42 of the tubular catheter shaft 26. The two anchor holes 44 are located within distal segment 42 of catheter shaft 26, such that each has a different longitudinal distance from the distal end 24 of the catheter shaft 26.

FIG. 4 is also a fragmentary perspective view of a distal segment of the catheter body 26 illustrating four anchor holes 46 located within the distal segment 42 of the tubular catheter shaft 26. The four anchor bore holes 46 are located within the distal segment 42 of the catheter shaft 26 where the first two of the anchor bore holes 46 are located equidistant longitudinally from the distal end 24 of the catheter shaft 26, and where the second two of the four anchor bore holes 46 are located equidistant longitudinally from the distal end 24 of catheter shaft 26.

FIG. 5 is a partial perspective view illustrating an alternative slot-shaped anchor hole 50 located within the distal segment 42 of the tubular catheter shaft 26. The distal segment 42, as illustrated in FIG. 4, is not shown in FIG. 5. From FIG. 5, it is clear that the anchor holes 32, 44, or 46 as shown in FIGS. 2–4, respectively, do not have to be circular in shape, but can be slotted as shown by anchor hole 50 in FIG. 5, or any other shape desired. Further, the relative location of the anchor holes with the distal segment 42 can be varied as desired.

FIG. 6 is a fragmentary cross section showing a slightly angled anchor hole 54 located within the distal segment 42 of the tubular catheter shaft 26. The anchor hole 54 has a longitudinal bore axis 52. Here, the perimeter 56 defines an angle θ/2 relative to the longitudinal bore axis 52. In addition, perimeter 58 also defines an angle θ/2 relative to the longitudinal bore axis 52. The angle defined between perimeter 56 and perimeter 58 is the angle θ.

FIG. 7 is a cross section of a distal segment of a catheter body 26 and tip 28. This alternative embodiment is similar to the embodiment of FIG. 2, however, the construction of the distal segment 42 is different. Here, the lumen 60 of the distal end 24 of catheter shaft 26 steps to a larger diameter at the proximal end of distal segment 42. The lumen 60 diameter then continuously increases distally to the distal end of the distal segment 42. Thus, the counterbore wall 62 and lumen 60 formed thereby slopes to a larger diameter from the proximal end of the distal portion 64 to the distal end of the catheter body 24.

FIG. 8 is a cross section of the catheter body 26 of the present invention illustrated as inserted into a mold assembly 70 to form a soft tip thereon. As shown in FIG. 1, the catheter shaft 26 has a proximal end 22 and a distal end 24 with a lumen 30 which extends longitudinally between the proximal end 22 and the distal end 24. The distal segment 42 of the tubular catheter shaft 26 has a counterbore along the axis of the lumen 30 within which the lumen 30 steps to a larger diameter. One or a plurality of anchor holes 32 are bored through the catheter body 26 within the distal segment 42 of the catheter body 26, where the holes extend generally perpendicular to the longitudinal axis of the catheter shaft 26. The anchor holes 32 provide the means for securing a soft tubular tip 28 as shown in FIG. 2 to the catheter shaft 26.

The distal end 24 of the catheter shaft 26 is inserted into the mold cavity 74. As shown in FIG. 8, all of the distal portion 42 is within the cavity, however, the distal end 24 of the catheter body is spaced from the end of the mold cavity 74 so that the tip distal of the end of the catheter body 24 can be formed. A pin 76 extends to a predetermined depth within the distal end 24 of catheter shaft 26 into the lumen 30. The pin diameter is substantially equal to the lumen diameter of catheter shaft 26. The mold cavity 74 can be heated to a predetermined elevated temperature where the temperature is below the melt temperature of the material of the catheter shaft 26.

A predetermined volume of material is injected into the mold cavity 74 through an injection port 72 around mandrel 76 until the mold cavity 74 is filled. A preferred material for the tip is a soft (25–50 D scale durometer) thermoplastic (PEBA). The soft tip is formed when the predetermined volume of material fills the mold cavity 74 to a predetermined distance beyond the distal end of catheter shaft 26. The predetermined volume of material also fills the counterbore 37 and protrudes into the anchor holes 32. The anchors shown in FIG. 2 are thus integrally formed with the tip in this preferred method of manufacture. The distal end 24 of the catheter shaft 26 is then removed from mold cavity 74 when the tip has cured or cooled sufficiently.

FIG. 9 is a fragmentary perspective view of a distal segment of catheter shaft 26 illustrating an alternative embodiment wherein catheter shaft 26 has a reduced diameter portion 78 including anchor hole 32. The material comprising the soft tubular tip 28 protrudes radially inward into anchor hole 32 in reduced diameter portion 78.

FIG. 10 is a partial cross section of catheter shaft 26 and tip 28 taken through the longitudinal plane bisecting anchor 33, further illustrating the alternative embodiment of FIG. 9 having reduced diameter portion 78. Anchor 33 protrudes radially inward into anchor hole 32 in reduced diameter portion 78.

FIG. 11 is a partial cross section of the catheter and mold assembly of the present invention, similar to FIG. 8, illustrating the method of forming the alternative embodiment tips of FIGS. 9 and 10 by injection molding, similar to the method discussed for FIG. 8. As shown in FIG. 9, distal segment 42 in this embodiment is reduced diameter portion 78 having anchor hole 32. The predetermined volume of material to be injected into mold cavity 74 through injection port 72 fills mold cavity 74 including reduced diameter portion 78 and anchor hole 32.

FIG. 12 is a fragmentary perspective view of a distal segment of catheter shaft 26 illustrating an alternative embodiment wherein catheter shaft 26 has a plurality of external longitudinal grooves or channels 80 and an external annular groove or channel 82. The soft tip material fills longitudinal grooves 80 forming a plurality of external longitudinal ribs (not shown). Soft tip material in communication with external longitudinal ribs further fills external annular groove 80 forming an external annular retaining ring (not shown). The distal edge of external annular groove 80 forms an annular distal groove shoulder 84. Tip 28 is held to catheter shaft 26 by the external longitudinal ribs formed in external longitudinal grooves 80, where said ribs are connected to annular retaining ring (not shown) formed in external annular groove 80, with the retaining ring overlapping and being held in place by annular groove distal shoulder 84.

It will be understood, that this disclosure is, in many respects, only illustrative. Changes may be made in details, particularly in matters of shape, size, material, numbers, and arrangement of parts without exceeding the scope of the invention. Accordingly, the scope of the invention is as defined within the language of the appended claims.

What is claimed is:

1. A catheter assembly for use as a guide catheter or diagnostic catheter comprising:

a generally elongate tubular catheter shaft having a proximal end and a distal end, with a radial wall defining a lumen extending longitudinally between the proximal end and the distal end, wherein a distal portion of the tubular catheter shaft has a counterbore therein along the axis of said lumen, said counterbore of a larger diameter than said lumen proximal of said distal portion of said tubular catheter shaft;

a tip having a proximal portion and a distal portion, forming a lumen in fluid communication with the lumen of the catheter body said proximal portion extending into the distal portion of the tubular catheter shaft with said distal portion of said tip extending distally beyond the distal end of the tubular catheter shaft, said distal portion of said tip having an outside diameter substantially equal to the outside diameter of the tubular catheter shaft, and an inside diameter substantially equal to the lumen diameter proximal of said distal portion of said tubular catheter shaft; and the tubular catheter shaft further having one or more anchor holes through said radial wall of said shaft within the distal portion thereof, wherein a portion of the material forming the lumen comprising said proximal portion of said tip extending into said distal portion of said tubular catheter shaft protrudes into said anchor holes for securing the tip to the tubular catheter shaft.

2. The catheter assembly of claim 1, wherein the tip is injection molded onto the distal portion of the tubular catheter shaft.

3. The catheter assembly of claim 1, wherein said lumen of the tubular catheter shaft steps to a larger diameter at a proximal end of the distal portion, then continuously increases distally to the distal end of the said distal portion.

4. The catheter assembly of claim 1, wherein the one or more anchor holes are spaced radially around the diameter of said distal portion.

5. The catheter assembly of claim 1, wherein two anchor holes are located within the distal portion of the tubular catheter shaft, each of said anchor holes being located at a different distance longitudinally from the distal end of the tubular catheter shaft.

6. The catheter assembly of claim 1, wherein the anchor hole is located within the distal portion of the tubular catheter shaft and said anchor hole has a slotted shape.

7. The catheter assembly of claim 1, wherein one or more anchor holes are located within the distal portion of the tubular catheter shaft, each anchor hole having an angled radial wall.

8. The tubular catheter shaft of claim 1 further containing a wire braid.

9. The catheter assembly of claim 1, wherein the tubular catheter shaft is formed of a relatively soft polymeric material.

10. The catheter assembly of claim 1, wherein the counterbore diameter in the distal portion is gradually increased distally to increase flexibility between the tubular catheter shaft and the tip.

* * * * *